(12) United States Patent
Shelton et al.

(10) Patent No.: US 9,327,075 B2
(45) Date of Patent: May 3, 2016

(54) METHODS AND APPARATUS FOR TRANSLATING A CONTINUOUS-DELIVER DELIVERY PROFILE INTO A PLURALITY OF PERIODIC BOLUS DELIVERIES

(71) Applicant: The Alfred E. Mann Foundation for Scientific Research, Santa Clarita, CA (US)

(72) Inventors: Brian M. Shelton, Pasadena, CA (US); Pedrum Minaie, Stevenson Ranch, CA (US); Jon Douglas Newbill, Simi Valley, CA (US); Peter C. Lord, Kihei, HI (US)

(73) Assignee: Medallion Therapeutics, Inc., Valencia, CA (US)

( * ) Notice: Subject to any disclaimer, the term of this patent is extended or adjusted under 35 U.S.C. 154(b) by 587 days.

(21) Appl. No.: 13/646,690

(22) Filed: Oct. 6, 2012

(65) Prior Publication Data
US 2013/0274709 A1    Oct. 17, 2013

Related U.S. Application Data

(63) Continuation of application No. 13/336,747, filed on Dec. 23, 2011, now Pat. No. 8,282,627, which is a continuation of application No. 12/329,476, filed on Dec. 5, 2008, now Pat. No. 8,096,987.

(51) Int. Cl.
*A61M 5/172* (2006.01)
*A61M 5/142* (2006.01)
*G06F 19/00* (2011.01)

(52) U.S. Cl.
CPC ........... *A61M 5/172* (2013.01); *A61M 5/14276* (2013.01); *G06F 19/3468* (2013.01); *A61M 2005/14208* (2013.01); *A61M 2205/3355* (2013.01); *A61M 2205/3523* (2013.01); *A61M 2205/50* (2013.01); *A61M 2205/52* (2013.01); *A61M 2209/01* (2013.01)

(58) Field of Classification Search
CPC ........... A61M 5/14276; A61M 5/172; A61M 2005/14208; A61M 2205/52; A61M 5/142; A61M 2205/3355; A61M 2205/3523; A61M 2205/50; A61M 2209/01; G06F 19/3468
USPC .............. 604/500, 151, 66, 67, 890, 1, 891.1, 604/507
See application file for complete search history.

(56) References Cited

U.S. PATENT DOCUMENTS

| | | | |
|---|---|---|---|
| 4,559,037 A * | 12/1985 | Franetzki et al. ............. | 604/151 |
| 7,109,878 B2 | 9/2006 | Mann et al. | |
| 8,096,987 B2 | 1/2012 | Shelton et al. | |
| 8,282,627 B2 | 10/2012 | Shelton et al. | |
| 2003/0051737 A1 * | 3/2003 | Hickle et al. ................. | 128/923 |
| 2005/0197649 A1 | 9/2005 | Shelton et al. | |

* cited by examiner

*Primary Examiner* — Kami A Bosworth
*Assistant Examiner* — Brandy S Lee
(74) *Attorney, Agent, or Firm* — Henricks, Slavin, Holmes LLP

(57) ABSTRACT

Methods and apparatus for translating a continuous-delivery delivery profile into a plurality of periodic bolus deliveries.

17 Claims, 13 Drawing Sheets

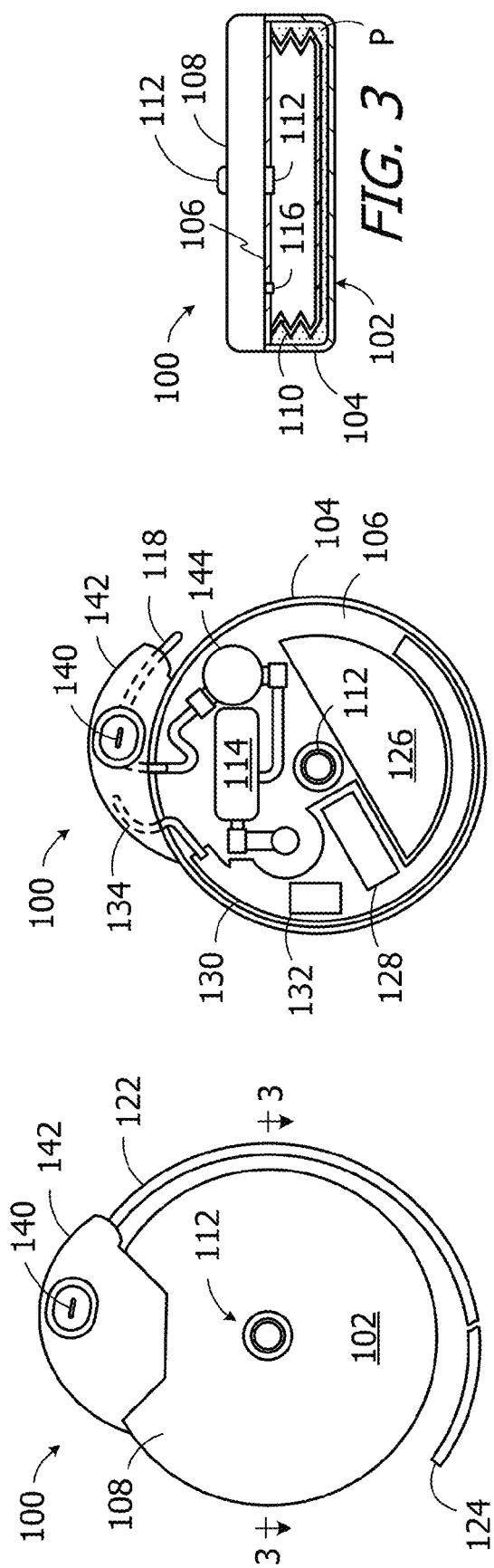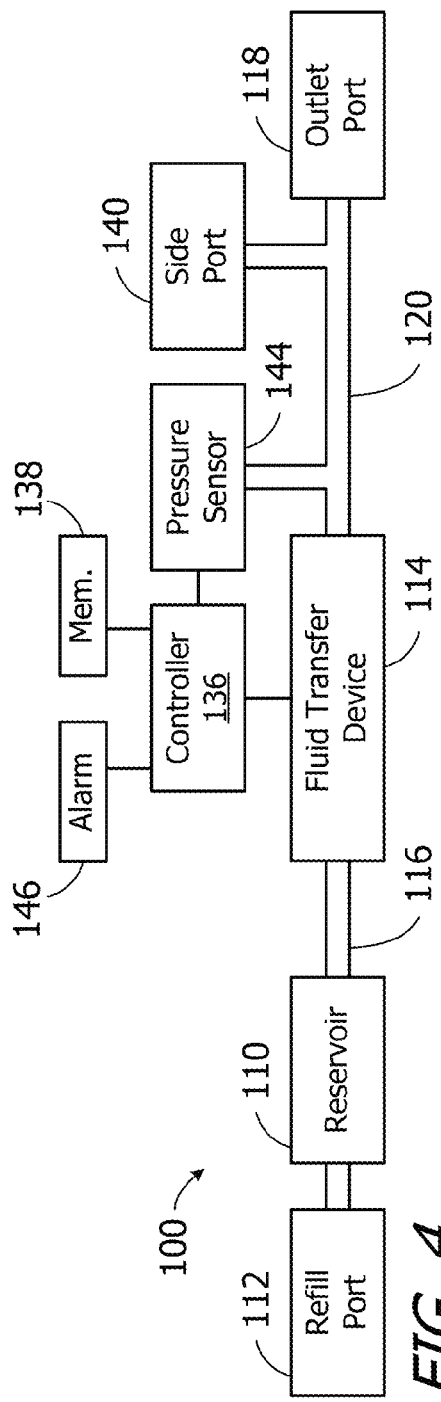

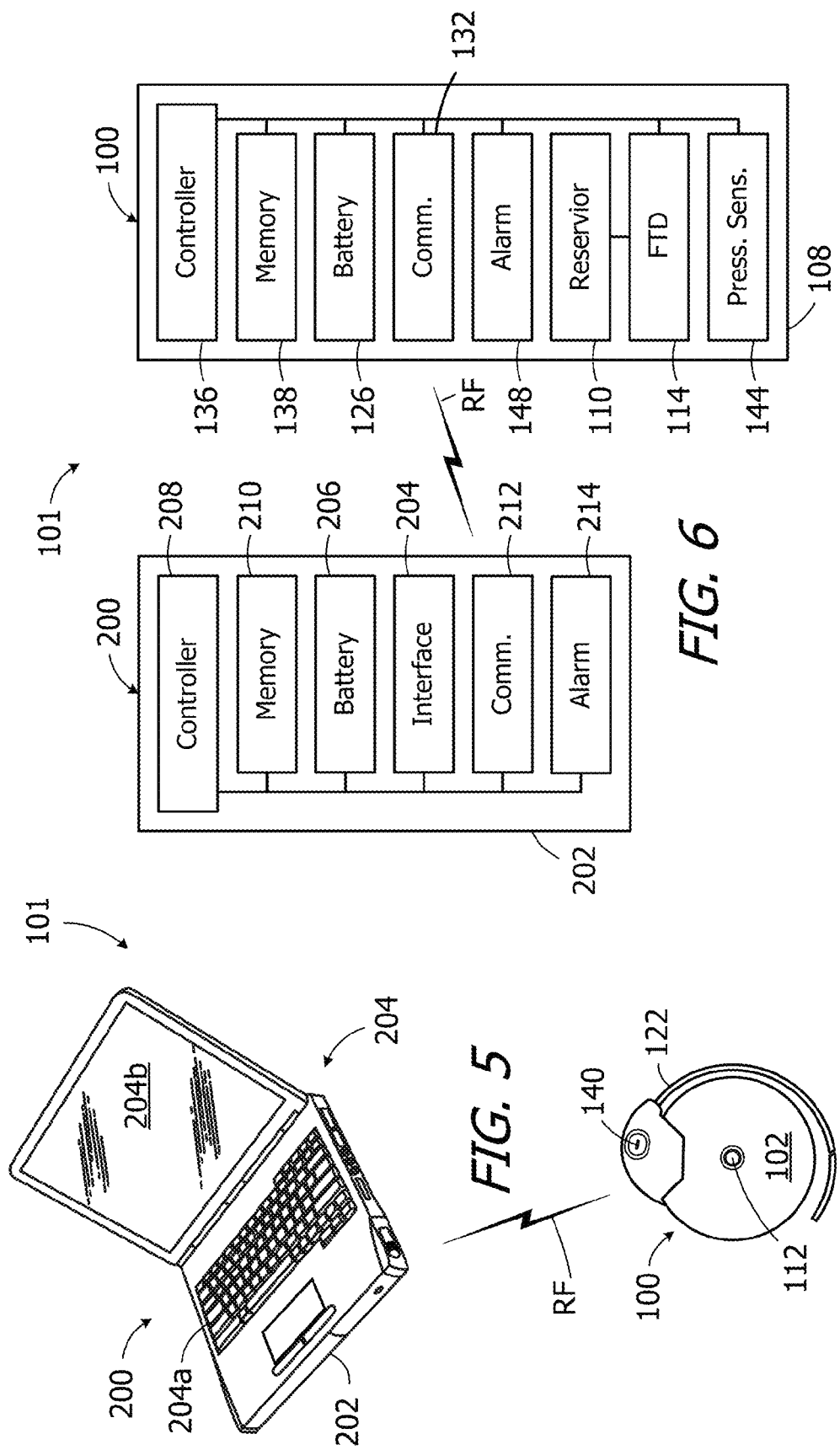

SAFETY/BOLUS SETTINGS

Drug Name: Drug 1
Concentration Unit: μg/mL
Maximum Concentration:
Maximum Daily Dose: μg/day
Maximum Rate: μg/hour
Is Drug Safe for PCA? Yes
Default Bolus (1 Bolus Per): 30 Min.

*FIG. 15*

METHODS AND APPARATUS FOR TRANSLATING A CONTINUOUS-DELIVER DELIVERY PROFILE INTO A PLURALITY OF PERIODIC BOLUS DELIVERIES

CROSS-REFERENCE TO RELATED APPLICATIONS

This application is a continuation of application Ser. No. 13/336,747, filed Dec. 23, 2011, now U.S. Pat. No. 8,282,627, which is a continuation of application Ser. No. 12/329,476, filed Dec. 5, 2008, now U.S. Pat. No. 8,096,476.

BACKGROUND OF THE INVENTIONS

1. Field of Inventions

The present inventions relate generally to ambulatory infusion devices.

2. Description of the Related Art

Ambulatory infusion devices, such as implantable infusion devices and externally carried infusion devices, have been used to provide a patient with a medication or other substance (collectively "infusible substance") and frequently include a reservoir and a pump. The reservoir is used to store the infusible substance and, in some instances, implantable infusion devices are provided with a fill port that allows the reservoir to be transcutaneously filled (and/or re-filled) with a hypodermic needle. The reservoir is coupled to the pump, which is in turn connected to an outlet port. A catheter, which has at least one outlet at the target body region, may be connected to the outlet port. As such, the infusible substance may be transferred from the reservoir to the target body region by way of the pump and catheter.

Ambulatory infusion devices frequently delivery the infusible substance in accordance with a continuous-delivery delivery profile that specifies one or more flow rates during the delivery profile cycle. Small volumes of infusible substance are delivered continuously. As used herein, "continuous" delivery means that (1) the fluid transfer device is actuated when fluid is scheduled to be delivered and (2) the fluid transfer device is physically capable of delivering the scheduled volume given its mechanical minimum. If, for example, a fluid transfer device is configured to deliver 0.25 microliter per actuation (partial actuations not being possible) and the continuous delivery profile calls for 0.25 microliter per minute, then continuous delivery would involve one actuation per minute. If, on the other hand, the same fluid transfer device was used in conjunction with a continuous delivery profile that called for 0.125 microliter per minute, then continuous delivery would involve one actuation every two minutes because the fluid transfer device is not capable of delivering 0.125 microliter. The continuous-delivery delivery profile is typically specified by a clinician and depends upon several factors including, but not limited to, the particular infusible substance formulation, the patient's condition, and the therapy being administered.

One issue that may, in some instances, be associated with the continuous delivery of an infusible substance is granuloma formation at the catheter outlet, especially in those instances where the patient is receiving a relatively high concentration of infusible substance over a relatively long period of time. A granuloma may partially or completely block the outlet, thereby preventing the patient from receiving the intended dosage of the infusible substance. Additionally, in the context of delivery to the intrathecal space, the formation of an inflammatory mass, or granuloma, may lead to spinal cord compression. One issue that may, in some instances, be associated with the delivery of small volumes of an infusible substance from a catheter into tissue is the failure of the infusible substance to disperse beyond the tissue that is close to the catheter outlet. Active protein drugs, such as neurotrophic factors, are examples of infusible substances that may have inadequate dispersion issues when delivered in small volumes from a catheter into tissue.

SUMMARY OF THE INVENTIONS

Methods and apparatus in accordance with at least one of the present inventions involve translating a continuous-delivery delivery profile into a plurality of periodic boluses. Such a translation reduces the likelihood of granuloma formation because the infusible substance is delivered periodically instead of continuously, and increases the likelihood that the infusible substance will adequately disperse because relatively large volumes are delivered over a short time when there is delivery, without adversely effecting the overall therapeutic intent of the delivery profile. In at least some implementations, the interval between the periodic boluses will as large as it can be, without losing the continuous therapeutic effect of the infusible substance, in order to maximize the volume effect of the periodic bolus.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of exemplary embodiments will be made with reference to the accompanying drawings.

FIG. 1 is a plan view of an implantable infusion device in accordance with one embodiment of a present invention.

FIG. 2 is a plan view of the implantable infusion device illustrated in FIG. 1 with the cover removed.

FIG. 3 is a partial section view taken along line 3-3 in FIG. 1.

FIG. 4 is a block diagram of the implantable infusion device illustrated in FIGS. 1-3.

FIG. 5 is a view of an implantable infusion device system in accordance with one embodiment of a present invention.

FIG. 6 is a block diagram of the implantable infusion device system illustrated in FIG. 5.

FIG. 15 is an illustration of an input screen that may be displayed in accordance with one embodiment of a present invention.

DETAILED DESCRIPTION OF THE EXEMPLARY EMBODIMENTS

Figure 9:
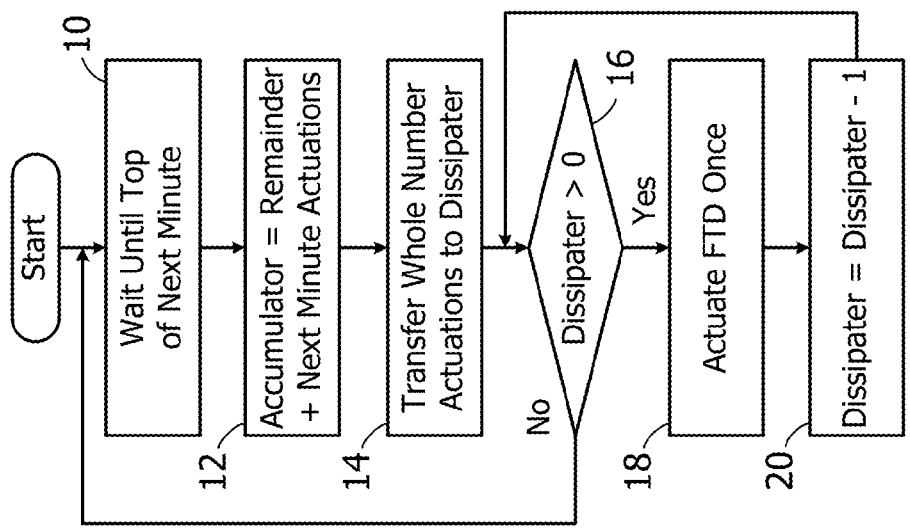
FIG. 9 is a flow chart in accordance with one embodiment of a present invention.

The following is a detailed description of the best presently known modes of carrying out the inventions. This description is not to be taken in a limiting sense, but is made merely for the purpose of illustrating the general principles of the inventions. The present inventions are also not limited to the exemplary implantable infusion devices described herein and, instead, are applicable to other implantable or otherwise ambulatory infusion devices that currently exist or are yet to be developed.

One example of an implantable infusion device in accordance with a present invention is generally represented by reference numeral 100 in FIGS. 1-4. As used herein, an "implantable infusion device" is a device that includes a reservoir and an outlet, and is sized, shaped and otherwise constructed (e.g. sealed) such that both the reservoir and outlet can be simultaneously carried within the patient's body. The exemplary infusion device 100 includes a housing 102 (e.g. a titanium housing) with a bottom portion 104, an internal wall 106, and a cover 108. An infusible substance (e.g. medication) may be stored in a reservoir 110 that is located within the housing bottom portion 104. The reservoir 110 may be replenished by way of a fill port 112 that extends from the reservoir, through the internal wall 106, to the cover 108. A hypodermic needle (not shown), which is configured to be pushed through the fill port 112, may be used to replenish the reservoir 110.

A wide variety of reservoirs may be employed. In the illustrated embodiment, the reservoir 110 is in the form of a titanium bellows that is positioned within a sealed volume defined by the housing bottom portion 104 and internal wall 106. The remainder of the sealed volume is occupied by propellant P, which may be used to exert negative pressure on the reservoir 110. Other reservoirs that may be employed in the present infusion devices include reservoirs in which propellant exerts a positive pressure. Still other exemplary reservoirs include negative pressure reservoirs that employ a movable wall that is exposed to ambient pressure and is configured to exert a force that produces an interior pressure that is always negative with respect to the ambient pressure.

The exemplary ambulatory infusion device 100 illustrated in FIGS. 1-4 also includes a fluid transfer device 114. The inlet of a fluid transfer device 114 is coupled to the interior of the reservoir 110 by a passageway 116, while the outlet of the fluid transfer device is coupled to an outlet port 118 by a passageway 120. Operation of the fluid transfer device 114 causes infusible substance to move from the reservoir 110 to the outlet port 118. A catheter 122 may be connected to the outlet port 118 so that the infusible substance passing through the outlet port will be delivered to a target body region in spaced relation to the infusion device 100 by way of the outlet 124 at the end of the catheter.

A wide variety of fluid transfer devices may be employed. In the illustrated embodiment, the fluid transfer device 114 is in the form of an electromagnet pump. The present inventions are not, however, limited to electromagnet pumps and may include other types of fluid transfer devices. Such devices include, but are not limited to, other electromagnetic pumps, solenoid pumps, piezo pumps, and any other mechanical or electromechanical pulsatile pump. Additionally, in the context of positive pressure reservoirs, the fluid transfer device may be in the form of an accumulator which includes a variable volume housing and active inlet and outlet valves. In the exemplary context of implantable drug delivery devices, and although the volume/stroke magnitude may be increased in certain situations, the fluid transfer devices will typically deliver about 1 microliter/stroke or other actuation, but may be more or less (e.g. about 0.25 microliter/actuation or less) depending on the particular fluid transfer device employed. A stroke will take about 3 milliseconds to complete in some electromagnet pumps. Additionally, although the exemplary fluid transfer device 114 is provided with internal valves (e.g. a main check valve and a bypass valve), valves may also be provided as separate structural elements that are positioned upstream of and/or downstream from the associated fluid transfer device.

Energy for the fluid transfer device 114, as well for other aspects of the exemplary infusion device 100, is provided by the battery 126 illustrated in FIG. 2. In the specific case of the fluid transfer device 114, the battery 126 is used to charge one or more capacitors 128, and is not directly connected to the fluid transfer device itself. The capacitor(s) 128 are connected to an electromagnet coil in the fluid transfer device 114, and disconnected from the battery 126, when the electromagnet coil is being energized, and are disconnected from the electromagnet coil and connected to the battery when the capacitor(s) are being recharged and/or when the fluid transfer device is at rest. The capacitor(s) 128 are carried on a board 130. A communication device 132, which is connected to an antenna 134, is carried on the same side of the board 130 as the capacitor(s) 128. The exemplary communication device 132 is an RF communication device. Other suitable communication devices include, but are not limited to, oscillating magnetic field communication devices, static magnetic field communication devices, optical communication devices, ultrasound communication devices and direct electrical communication devices.

A controller 136 (FIG. 4), such as a microprocessor, microcontroller or other control circuitry, is carried on the other side of the board 130. The controller controls the operations of the infusion device 100 in accordance with instructions stored in memory 138 and/or provided by an external device (e.g. the clinician's programming unit 200 described below) by way of the communication device 132. For example, the controller 136 may be used to control the fluid transfer device 114 to supply fluid to the patient in accordance with, for example, a stored continuous-delivery delivery profile or a patient/clinician initiated bolus delivery request. Although the present inventions are not limited to any particular delivery profiles, one example of a stored continuous-delivery delivery profile is discussed below with reference to FIGS. 7 and 8. The controller 136 may also be used to translate a stored continuous-delivery delivery profile into a plurality of period bolus deliveries, as is discussed below with reference to FIGS. 10 and 11.

Referring to FIGS. 1, 2 and 4, the exemplary infusion device 100 is also provided with a side port 140 that is connected to the passageway 120 between the outlet of the fluid transfer device 114 and the outlet port 118. The side port 140 facilitates access to an implanted catheter 122, typically by way of a hypodermic needle. For example, the side port 140 allows clinicians to push fluid into the catheter 122 and/or draw fluid from the catheter for purposes such as checking catheter patency, sampling CSF, injecting contrast dye into the patient and/or catheter, removing medication from the catheter prior to dye injection, injecting additional medication into the region at the catheter outlet 124, and/or removing pharmaceuticals or other fluids that are causing an allergic or otherwise undesirable biologic reaction.

The outlet port 118, a portion of the passageway 120, the antenna 134 and the side port 140 are carried by a header assembly 142. The header assembly 142 is a molded, plastic structure that is secured to the housing 102. The housing 102 includes a small aperture through which portions of the passageway 120 are connected to one another, and a small aperture through which the antenna 134 is connected to the board 130.

The exemplary infusion device 100 illustrated in FIGS. 1-4 also includes a pressure sensor 144 that is connected to the passageway 120 between the outlet of the fluid transfer device 114 and the outlet port 118. As such, the pressure sensor 144 senses the pressure at the outlet port 118 which, in the illustrated embodiment, is also the pressure within the catheter 122. The pressure sensor 144 is connected to the controller 136 and may be used to analyze a variety of aspects of the operation of the exemplary implantable infusion device 100. For example, pressure measurements may be used by the controller 136 to determine whether or not there is a blockage in the catheter 122 and/or whether or not the fluid transfer device 114 is functioning properly. The controller 136 may perform a variety of different functions in response to a determination that the fluid transfer device 114 is not functioning properly or a determination that the catheter 122 is blocked. For example, the controller 136 may actuate an audible alarm 146 that is located within the housing 102 in order to signal that the fluid transfer device 114 is not functioning properly or the catheter 122 is blocked.

Turning to FIGS. 5 and 6, the exemplary implantable infusion device 100 may be included in an infusion device system 101 that also includes a clinician's programming unit 200 that is not implanted in the patient. The exemplary clinician's programming unit 200 is a notebook that includes a housing 202, a user interface 204 (e.g., a keyboard 204a/display 204b, or a touch screen), a battery or other power source 206, a controller 208, such as a microprocessor, microcontroller or other control circuitry, memory 210, and a communication device 212 (including an antenna if necessary). Although the present inventions are not limited to any particular communication device, the exemplary communication device 212 is a telemetry device that transmits an RF signal at a specified frequency. The RF signal may, in some instances, be a carrier signal that carries bit streams. The communication device 212 is configured to send signals to and receive signals from the communication device 132 in the implantable infusion device 100 by way of the antenna 134. Other exemplary communication devices include oscillating magnetic field communication devices, static magnetic field communication devices, optical communication devices, ultrasound communication devices and direct electrical communication devices. In some instances, the clinician's programming unit may also include an audible alarm 214.

The exemplary clinician's programming unit 200 may be used to perform a variety of conventional control functions including, but not limited to, turning the infusion device ON or OFF and programming various infusion device parameters. Examples of such parameters include, but are not limited to, the rate of delivery of a given medication, the time at which delivery of a medication is to commence, and the time at which delivery of a medication is to end. For example, the clinician's programming unit 200 may be used to configure a delivery profile, such as a continuous-delivery delivery profile, and to translate, or instruct the implantable infusion device 100 to translate, a continuous-delivery delivery profile into a plurality of periodic bolus deliveries. Additionally, in at least some implementations, the implantable infusion device 100 will transmit signals to the clinician's programming unit 200. The signals provide status information about the infusion device 100 that may be stored in memory 210 and/or displayed on the display 204b. Examples of such status information include, but are not limited to, the state of charge of the battery 126, the amount of medication remaining in the reservoir 110, the amount of medication that has been delivered during a specified time period, and the presence of a catheter blockage. The signals from the infusion device 100 may also be indicative of sensed physiological parameters in those instances where the infusion device is provided with physiological sensors (not shown).

Figure 7:
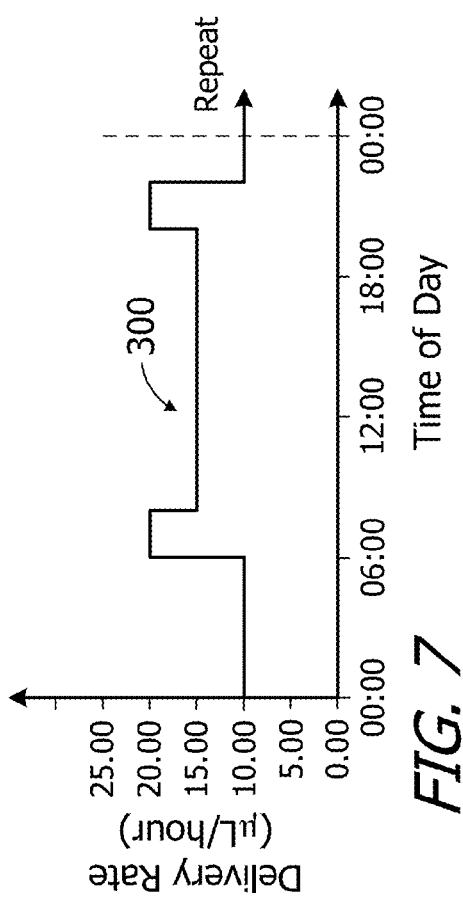
FIG. 7 is a graphical illustration of one example of a continuous-delivery delivery profile.
Figure 8:
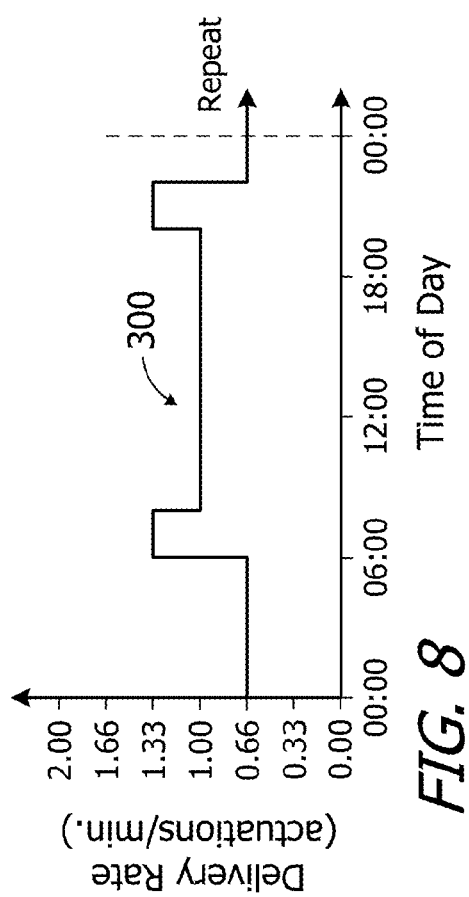
FIG. 8 is a graphical illustration of one example of a continuous-delivery delivery profile.

One example of a continuous-delivery delivery profile is represented by reference numeral 300 in FIG. 7. Exemplary profile 300, which has a twenty-four hour cycle time and may be expressed in terms of the volume delivered per hour as illustrated in FIG. 7, specifies that the infusible substance is to be delivered at a rate of 10 microliters/hour (µL/hour) from 00:00 to 06:00 hours, at a rate of 20 µL/hour from 06:00 to 08:00, at a rate of 15 µL/hour from 08:00 to 20:00, at a rate of 20 µL/hour from 20:00 to 22:00, and at a rate of 10 µL/hour from 22:00 to 24:00. In one exemplary implementation, each actuation is a pump stroke that takes about 3 milliseconds to complete and results in the delivery of 0.25 µL of infusible substance to the patient. Accordingly, when expressed in terms of actuations per minute in the manner illustrated in FIG. 8, the exemplary profile 300 specifies that the infusible substance is to be delivered at a rate of 0.66 actuations/minute from 00:00 to 06:00 hours, at a rate of 1.33 actuations/minute from 06:00 to 08:00, at a rate of 1.0 actuation/minute from 08:00 to 20:00, at a rate of 1.33 actuations/minute from 20:00 to 22:00, and at a rate of 0.66 actuations/minute from 22:00 to 24:00. The conversion from volume per hour to actuations per minute may be performed by the implantable medical device controller 136 and/or by the clinician's programming unit controller 208. For example, the clinician may input weight-based dosages of a drug that the patient is to receive at various portions of the profile, e.g. dosages expressed in milligrams (mg) per hour, as well as the drug concentration of the associated with the infusible substance, e.g. concentration expressed in milligrams per milliliter (mg/mL). The concentration may be used to convert the weight-based dosages into volume-based dosages, which may then be converted, either by the implantable medical device controller 136 or the clinician's programming unit controller 208, into actuation-based dosages.

One example of a control method that may be employed by the implantable medical device controller 136 to execute a stored delivery profile, such as the continuous-delivery delivery profile 300, is illustrated in FIG. 9. The control method actuates the associated fluid transfer device (e.g. fluid transfer device 114), when appropriate, at the top (i.e. beginning) of each minute. If, for example, two pump strokes or other fluid transfer device actuations are required per minute to maintain the requisite flow rate, those actuations will occur at the top of each minute.

Accordingly, the first step in the exemplary method illustrated in FIG. 9 is to wait until the top of the minute to proceed (Step 10). The second step is add the actuations associated with this minute to a remainder, if any, in an accumulator (Step 12). If, for example, the rate associated with the minute was 1.33 actuations/minute, then 1.33 actuations would be added to the accumulator. Next, the whole number of actuations in the accumulator is transferred to a dissipater (Step 14). If, for example, 1.33 actuations were in the accumulator, then 1 actuation would transferred to the dissipater and there would be a remainder of 0.33 actuations in the accumulator. The fluid transfer device is then actuated once, and the dissipater is decremented by one actuation so long as there are actuations in the dissipater (Steps 16, 18 and 20).

A continuous-delivery delivery profile, such as the delivery profile 300, may be translated into a plurality of periodic bolus deliveries by the implantable medical device controller 136 and/or by the clinician's programming unit controller 208. For example, a 24-hour cycle may be thought of as 24 one-hour intervals and each periodic bolus may take place at some point during an interval, with no delivery during the remainder of the interval. The translation may be, for example, retrospective or prospective. In a retrospective translation, the fluid transfer device is not actuated during an interval in accordance with the delivery profile schedule for that particular interval. At the end of the interval, the fluid transfer device is controlled to deliver the entire quantity of infusible substance that would have been delivered during the interval, in accordance with the delivery profile, during the beginning of the next interval. In a prospective translation, the fluid transfer device is controlled to deliver the entire quantity of infusible substance that is scheduled to be delivered in accordance with the delivery profile during each interval at the beginning of each interval. The fluid transfer device is not actuated in accordance with the delivery profile during the remainder of the interval. In other exemplary translations, the boluses may be initiated at a time which insures that the bolus deliveries will end at the end of the associated intervals. In still other exemplary translations, boluses may begin after the beginning of the associated intervals and end prior to the end of the associated intervals.

The duration of the interval will depend upon the infusible substance and the location to which it is delivered. The interval between the periodic boluses may be as large as it can be, without losing the continuous therapeutic effect of the infusible substance, in some instances in order to maximize the volume effect of the periodic bolus. For example, the maximum interval may be as short as 5 minutes in the context of fentanyl delivered to the blood, may be as long as 12 hours or more in some therapies, and may be any duration therebetween in other therapies.

Figure 10:
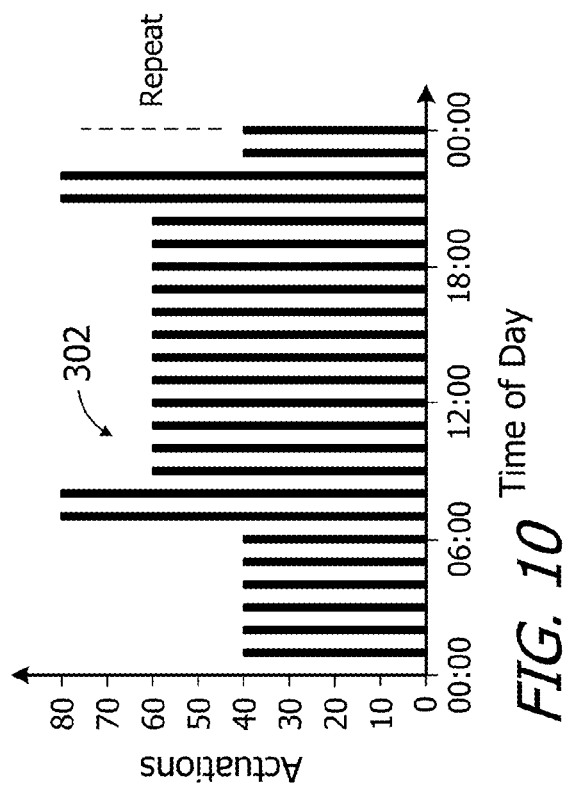
FIG. 10 is a graphical illustration of one example of a periodic bolus delivery in accordance with one embodiment of a present invention.

As illustrated in FIG. 10, in one exemplary translation, the continuous-delivery delivery profile 300 (FIGS. 7 and 8) may be translated into a plurality of periodic boluses 302 that are delivered immediately after the end of one-hour intervals. The translation is retrospective and, accordingly, the actuations that would have occurred during each one-hour interval are delivered at the beginning of the next interval. For example, the exemplary profile 300 specifies that, during the one-hour interval that begins at 00:00 and ends at 01:00, the infusible substance is scheduled to be delivered at a rate of 0.66 actuations/minute. Thus, over the course of this particular interval, the exemplary profile 300 specifies that the fluid transfer device should be actuated 39.6 times. In those instances where the fluid transfer device is not configured for fractional actuations, the fluid transfer device will be actuated 39 times immediately after the end of the one-hour interval. If, for example, the fluid transfer device actuations take 3 milliseconds and the fluid transfer device delivers 0.25 µL/actuation, then the patient will receive a bolus which consists of 9.75 µL and is delivered during the first second of the next one-hour interval.

Figure 11:
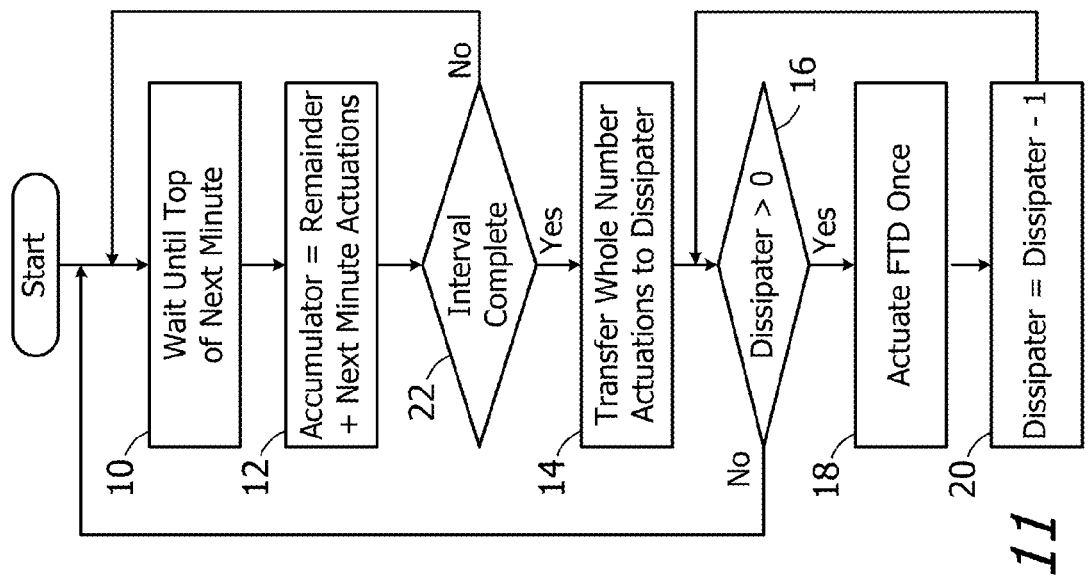
FIG. 11 is a flow chart in accordance with one embodiment of a present invention.

One example of a control method that may be employed by the implantable medical device controller 136, or by the clinician's programming unit controller 208, to translate a stored continuous-delivery delivery profile, such as delivery profile 300, into a plurality of periodic boluses is illustrated in FIG. 11. The control method is similar to that illustrated in FIG. 9. Here, however, the associated fluid transfer device (e.g. fluid transfer device 114) is not actuated in accordance with the continuous-delivery delivery profile 300 until after the end of each of a plurality of intervals. To that end, the first two steps in the exemplary method illustrated in FIG. 11 correspond to those of the method illustrated in FIG. 9. After waiting until the top of each minute to proceed (Step 10), the actuations associated with this minute are added to a remainder, if any, in the accumulator (Step 12). The remainder of the steps will not occur, however, until after the end of the next bolus interval. The actuations associated with subsequent minutes will, instead, be added to the remainder in the accumulator during the interval (Steps 22, 10 and 12). After the interval is complete, the whole number of actuations in the accumulator will be transferred to a dissipater (Step 14) and the above-described actuation/dissipation cycle will continue until there are no actuations remaining in the dissipater (Steps 16-20). It should be noted that the method illustrated in FIG. 11 accommodates periodic bolus deliveries that last more than one minute, should such a situation occur, by simply accumulating actuations in the accumulator for the next periodic bolus delivery (Steps 10, 12 and 22) while the actuation/dissipation cycle associated with the current periodic bolus delivery proceeds.

It should be emphasized that the presented inventions are not limited to use in conjunction with continuous-delivery delivery profiles that have continuous delivery over an entire 24-hour cycle. Continuous-delivery delivery profiles that have cycle times of more, or less, than 24 hours may be translated into a plurality of period bolus deliveries. In addition, continuous-delivery delivery profiles that have periods of non-delivery may be translated into a plurality of periodic boluses followed (or preceded) by periods of non-delivery. For example, a 24-hour cycle with three sub-cycles that each include 6 hours of continuous delivery followed by 2 hours of non-delivery may be translated, assuming a 1-hour bolus interval, into a 24-hour cycle with three sub-cycles that each include 6 periodic bolus deliveries at 1-hour intervals followed 2 hours of non-delivery.

Figure 12:
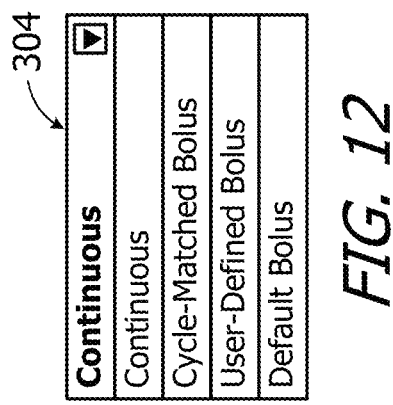
FIG. 12 is an illustration of a menu that may be displayed in accordance with one embodiment of a present invention.

The present inventions are not limited to any particular apparatus or methods for translating a continuous-delivery delivery profile into a plurality of periodic bolus deliveries, and/or presenting translation choices to the clinician and/or receiving related instructions from the clinician. For example, the clinician's programming unit 200 (FIG. 5) may display, among other things, a delivery mode pull-down menu 304 such as that illustrated in FIG. 12 on the display 204*b*. Here, the clinician may select from one of the following modes of delivering the infusible substance in accordance with a stored continuous-delivery delivery profile: Continuous, Cycle-Matched Bolus, User-Defined Bolus and Default Bolus. The selected mode appears near the pull-down button. When the Continuous mode is selected, the infusible substance will simply be delivered in accordance with the continuous-delivery delivery profile without translation in, for example, the manner described above with reference to FIGS. 7-9.

Figure 13:
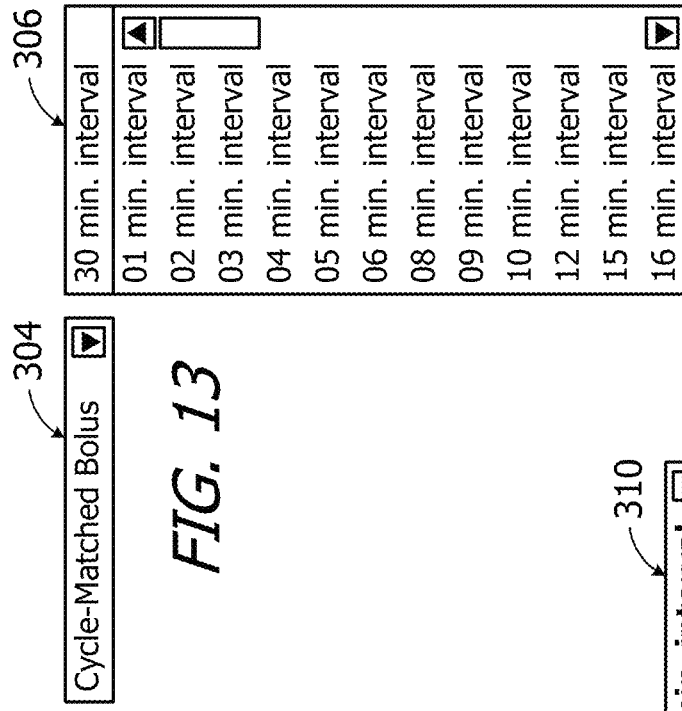
FIG. 13 is an illustration of a menu that may be displayed in accordance with one embodiment of a present invention.

Turning to FIG. 13, an interval pull-down menu 306 may be presented adjacent to the delivery mode pull-down menu 304 on the clinician's programming unit display 204*b* when the Cycle-Matched Bolus mode is selected with the delivery mode pull-down menu 304. The interval pull-down menu 306 allows the clinician to select from a plurality of bolus intervals that will result in a whole number of boluses being delivered per cycle, at the same points in time during each cycle, when the associated continuous-delivery delivery profile is translated into a plurality of periodic boluses. If, for example, the continuous-delivery delivery profile that has a 24-hour cycle (1440-minute cycle) such as that illustrated in FIGS. 7 and 8, then the clinician may be presented with an interval pull-down menu that allows the clinician to selection from some or all of the following predefined minute-based intervals: 1, 2, 3, 4, 5, 6, 8, 9, 10, 12, 15, 16, 18, 20, 24, 30, 32, 36, 40, 45, 48 and 60; and/or some or all of the following predefined hour-based intervals: 1, 2, 3, 4, 6, 8, 12 and 24. The selection of, for example, a 30-minute interval would result in a bolus being delivered every 30 minutes, or 48 times over the course of the 24-hour cycle.

Certain safety features may also be incorporated into the Cycle-Matched Bolus mode. For example, the intervals presented may be limited to those which do not create a conflict with other criteria (e.g. maximum rate per hour or maximum single bolus dosage) associated with the particular infusible substance. Alternatively, in those instances where the interval selection is not limited, the clinician may be presented with an error message and/or forced to make another selection, when the selected interval creates a conflict with other criteria.

Figure 14:
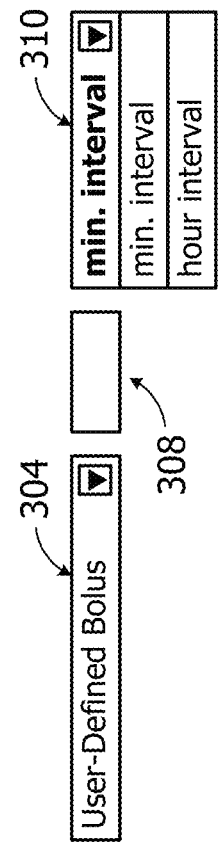
FIG. 14 is an illustration of a menu that may be displayed in accordance with one embodiment of a present invention.

Alternatively, as illustrated in FIG. 14, an input box 308 and a minutes/hours pull-down menu 310 may be presented adjacent to the delivery mode pull-down menu 304 on the clinician's programming unit display 204*b* when the User-Defined Bolus mode is selected with the delivery mode pull-down menu 304. The clinician is free to input any time-based interval, subject to the safety issues discussed below, using the input box 308 and minutes/hours pull-down menu 310. The interval need not result in a whole number of boluses being delivered per cycle, at the same points in time during each cycle, when the associated continuous-delivery delivery profile is translated into a plurality of periodic boluses. For example, a user-defined interval of five hours would result in the boluses being delivered at different times each day if the continuous-delivery delivery profile has a 24-hour cycle. In some implementations, the clinician may be provided with information (e.g. through the use of a pop-up window) concerning the available range of acceptable intervals.

Certain safety features may also be incorporated into the User-Defined Bolus mode. If, for example, the clinician inputs an interval which creates a conflict with other criteria (e.g. maximum rate per hour or maximum single bolus dosage), the clinician may be presented with an error message and/or forced to make another selection.

The Default Bolus mode allows the clinician to select a bolus interval that has been previously defined. For example, a default bolus interval may be set for a particular drug or other infusible substance when inputting other information about that substance, and the default bolus interval will be employed when the Default Bolus mode is selected on the delivery mode menu 304. One example of an input screen 312 that may be displayed by the clinician's programming unit 200 and allows the clinician to set a Default Bolus interval when inputting other information about the infusible substance is illustrated in FIG. 15.

Certain safety features may also be incorporated into the User-Defined Bolus mode. For example, the intervals presented may be limited to those which do not create a conflict with other criteria (e.g. maximum rate per hour or maximum single bolus dosage) associated with the particular infusible substance. Alternatively, in those instances where the interval selection is not limited, the clinician may be presented with an error message and/or forced to make another selection, when the selected interval creates a conflict with other criteria.

It should be noted here that the periodic bolus delivery modes described above need not interfere with clinician or patient initiated bolus ("CPI bolus") requests. If a CPI bolus request occurs during a periodic bolus, then the CPU bolus will be delivered immediately after the periodic bolus. For example, the actuations associated with the CPI bolus request may be added to the dissipater so that they will occur immediately after the actuations associated with the periodic bolus have been dissipated. If on the other hand, a CPI bolus request occurs between periodic bolus deliveries, then the CPI bolus will be delivered when requested. The CPI bolus will not, however, be added to periodic bolus or be delivered between boluses if such delivery would create a conflict with other criteria (e.g. maximum rate per hour or maximum single bolus dosage). An audible or visible notification may be provided to alert the patient or clinician that the CPI bolus will not be delivered due the conflict. Alternatively, the CPI bolus could be automatically reduced to maximum allowed under the circumstances. Here too, an audible or visible notification may be provided.

The exemplary clinician's programming unit 200 may also be used to generate and display graphical representations of continuous-delivery delivery profiles and/or periodic bolus deliveries that are based on, for example, translated continuous-delivery delivery profiles. In addition to providing information in concerning the deliveries in a readily comprehensible manner, at least some of the graphical representations displayed by the clinician's programming unit 200 may be manipulated by the clinician and, through such manipulation, aspects of the continuous-delivery delivery profiles and/or periodic bolus deliveries that are based on, for example, translated continuous-delivery delivery profiles may be adjusted.

Figure 16:
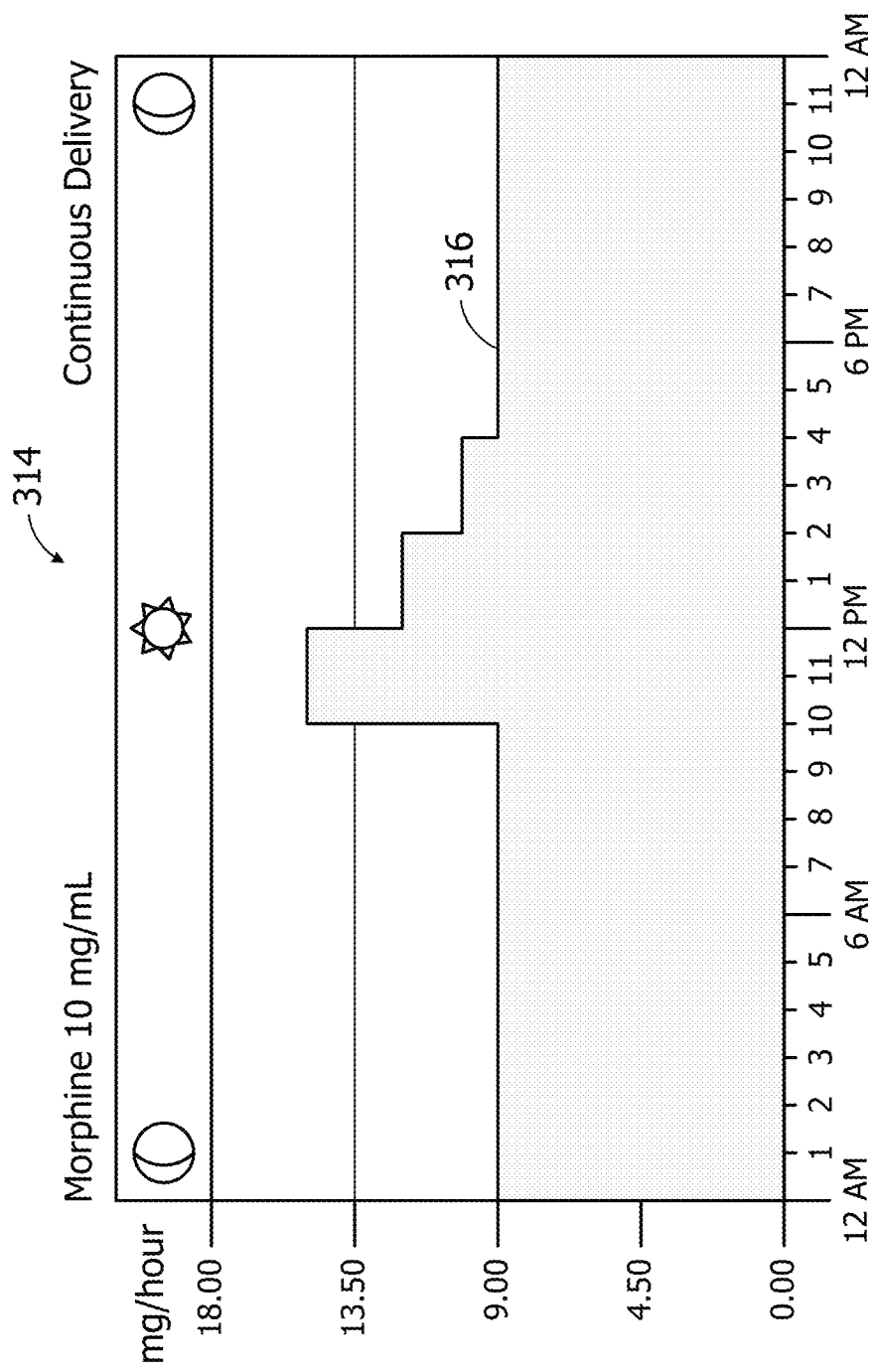
FIG. 16 is a graphical representation of a continuous-delivery delivery profile that may be displayed in accordance with one embodiment of a present invention.

Referring first to FIG. 16, the exemplary clinician's programming unit 200 may be used to generate and display (e.g. with the controller 208 and display 204*b*) a graph 314 for a particular infusible substance and a representation 316 of a continuous-delivery delivery profile associated with the infusible substance. The exemplary profile representation 316 consists of a colored (e.g. gray) area that provides readily decipherable representation of the delivery rates at all times during the displayed profile.

The delivery profile representation 316 may also be employed, in combination with additional graphical information, after the associated continuous-delivery delivery profile has been translated into a plurality of periodic bolus deliveries. To that end, and referring to FIG. 17, a plurality of bolus markers 318 may be placed over the delivery profile representation 316 to show when the periodic bolus deliveries will occur. The exemplary bolus markers 318 are in the form of vertical lines. However, any suitable indicia may be employed. By simply looking at the graphical illustration, the clinician will be able to readily ascertain the bolus interval (here, 30 minutes) and should be able to quickly calculate the amount of drug to be delivery in any particular bolus (e.g. 4.5 mg at 4 AM). Moreover, in at least some implementations, when the pointer 320 is positioned for a few seconds over a particular bolus marker 318, a pop-up window 322 will appear with information about the associated bolus (e.g. time point in the cycle, drug amount and interval).

Figure 17:
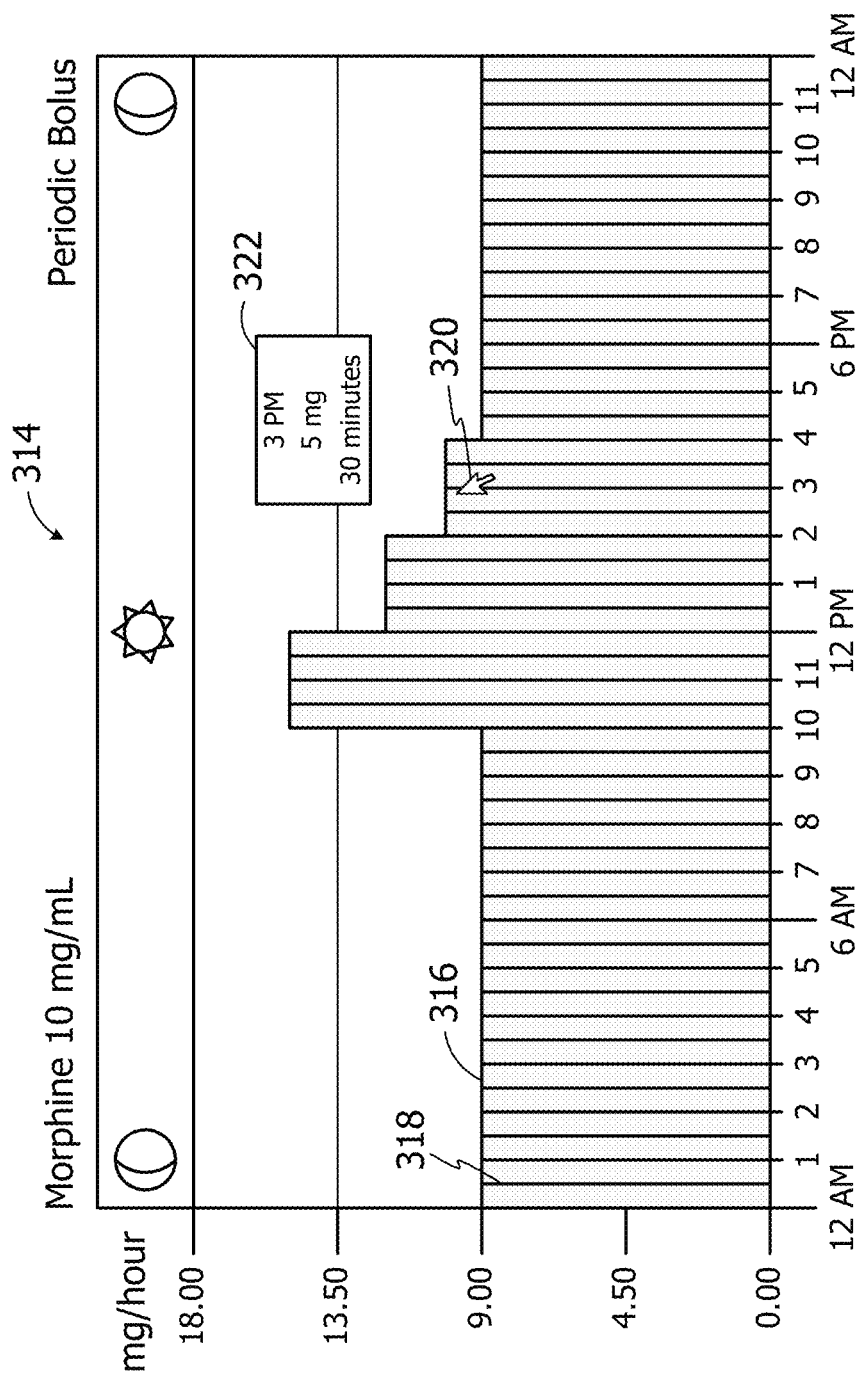
FIG. 17 is a graphical representation of a continuous-delivery delivery profile and a plurality of periodic bolus deliveries that may be displayed in accordance with one embodiment of a present invention.
Figure 18:
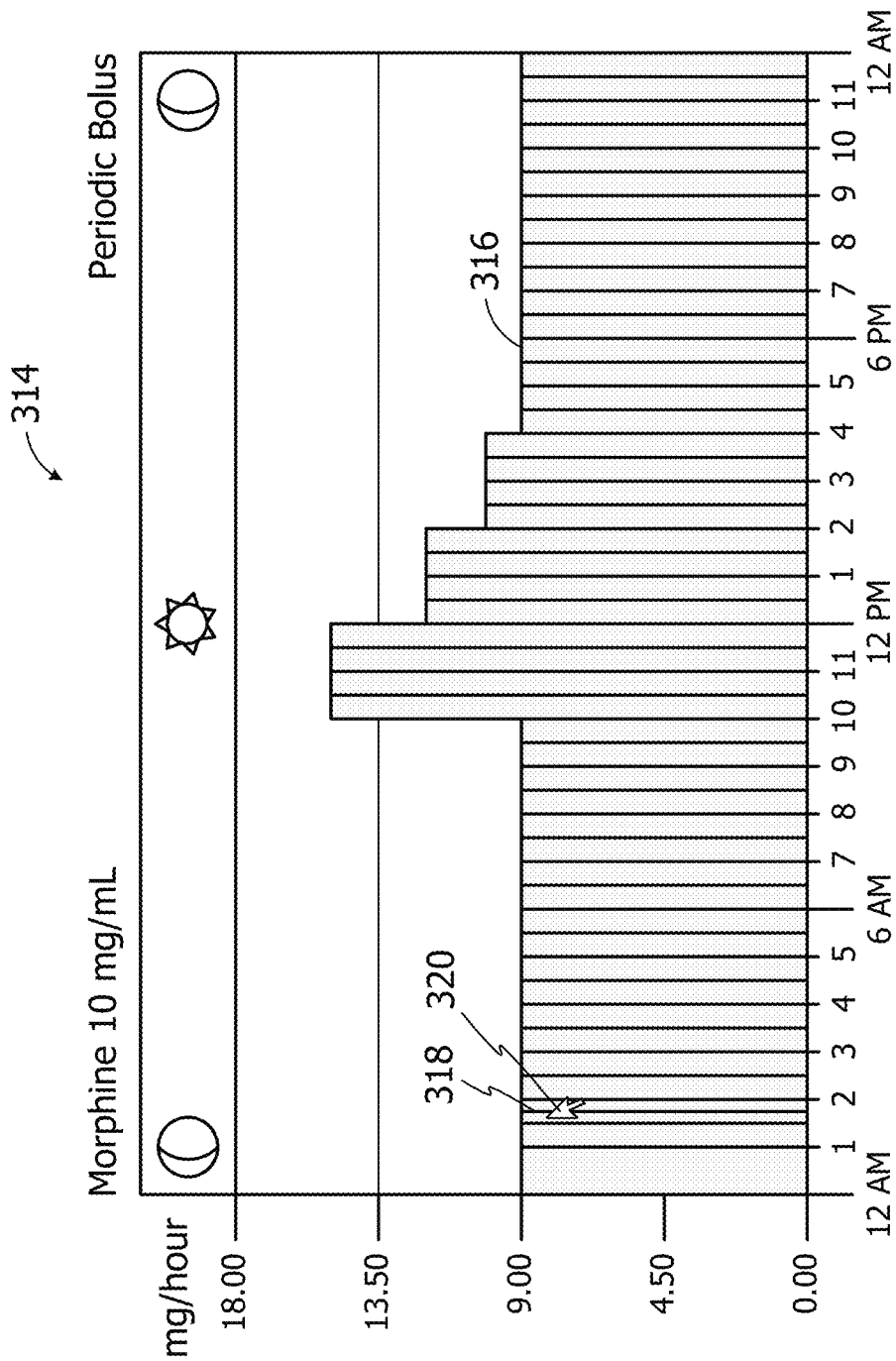
FIG. 18 is a graphical representation of a continuous-delivery delivery profile and a plurality of periodic bolus deliveries that may be displayed in accordance with one embodiment of a present invention.
Figure 19:
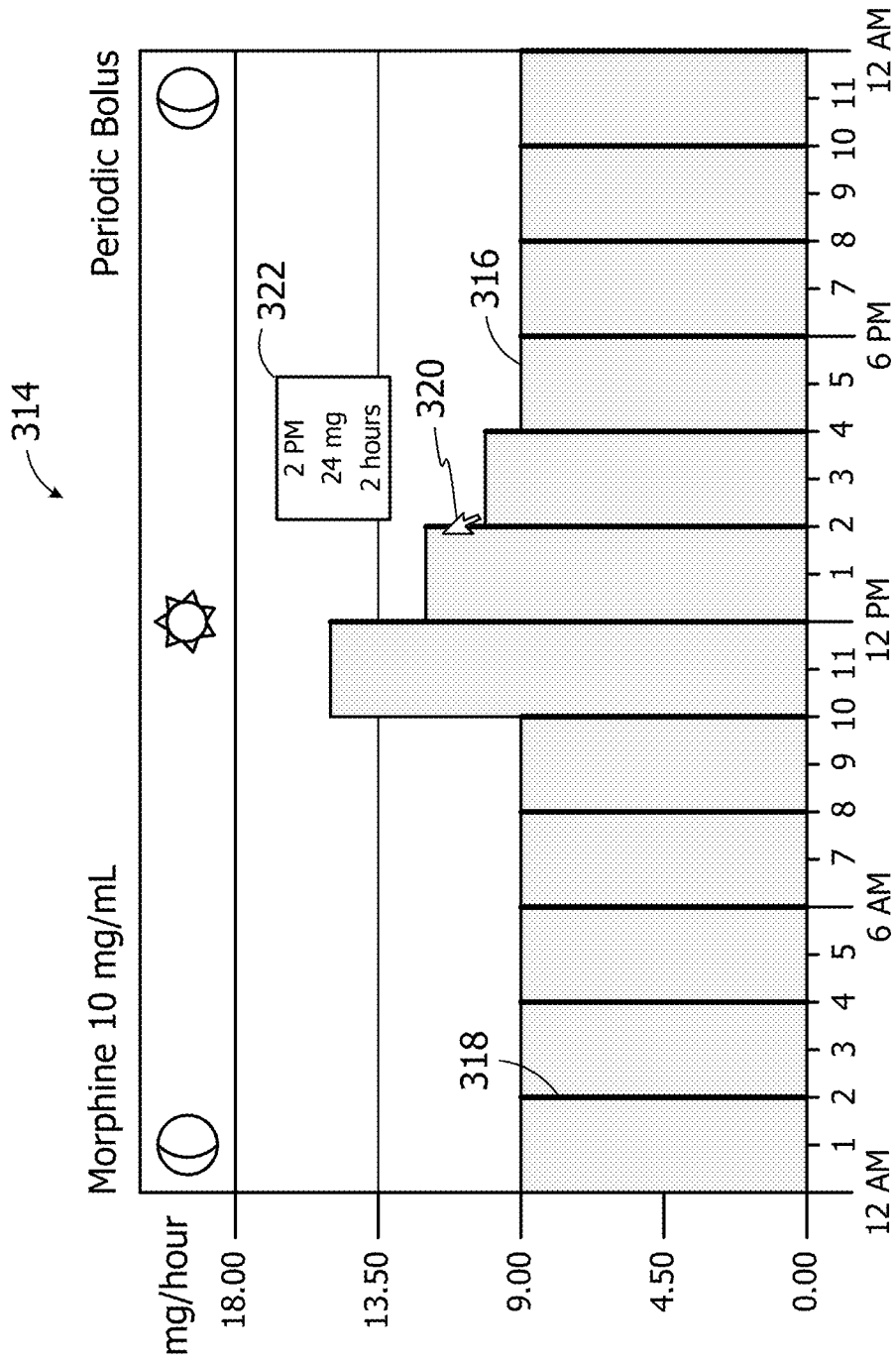
FIG. 19 is a graphical representation of a continuous-delivery delivery profile and a plurality of periodic bolus deliveries that may be displayed in accordance with one embodiment of a present invention.

Turning to FIG. 18, graphical representations of translated delivery profiles such as that illustrated in FIG. 17 may also be used to adjust the periodic delivery or otherwise re-translate the associated continuous-delivery delivery profile. The pointer 320 may, for example, be used to drag one of the bolus markers 318 to the right, thereby increasing the interval between that bolus marker and the prior (in time) bolus marker. In the illustrated representation, the bolus marker 318 that was originally located at the 12:30 AM position in the graphical representation is in the process of being moved to the 2:00 AM position by, for example, moving a mouse while depressing a button on the mouse, thereby increasing the interval between that bolus delivery and the prior bolus delivery from 30 minutes to 2 hours. After the bolus marker 318 reaches the 2:00 AM position and the mouse button is released, the graphical representation will be changed to represent the new 2 hour bolus interval and, as is illustrated for example in FIG. 19. It should be noted here that selecting (or reselecting) the bolus interval in this manner is subject to the same limitations described above with reference to FIGS. 12-15. If for example, the selected delivery mode is the Cycle-Matched Bolus mode, then the clinician will only be able to move the bolus marker 318 to a point in time that will result in a whole number of boluses being delivered per cycle, at the same points in time during each cycle. Additionally, if the newly selected interval creates a conflict with other criteria (e.g. maximum single bolus dosage) associated with the particular infusible substance, then the clinician may be presented with an error message and/or forced to make another selection.

Figure 20:
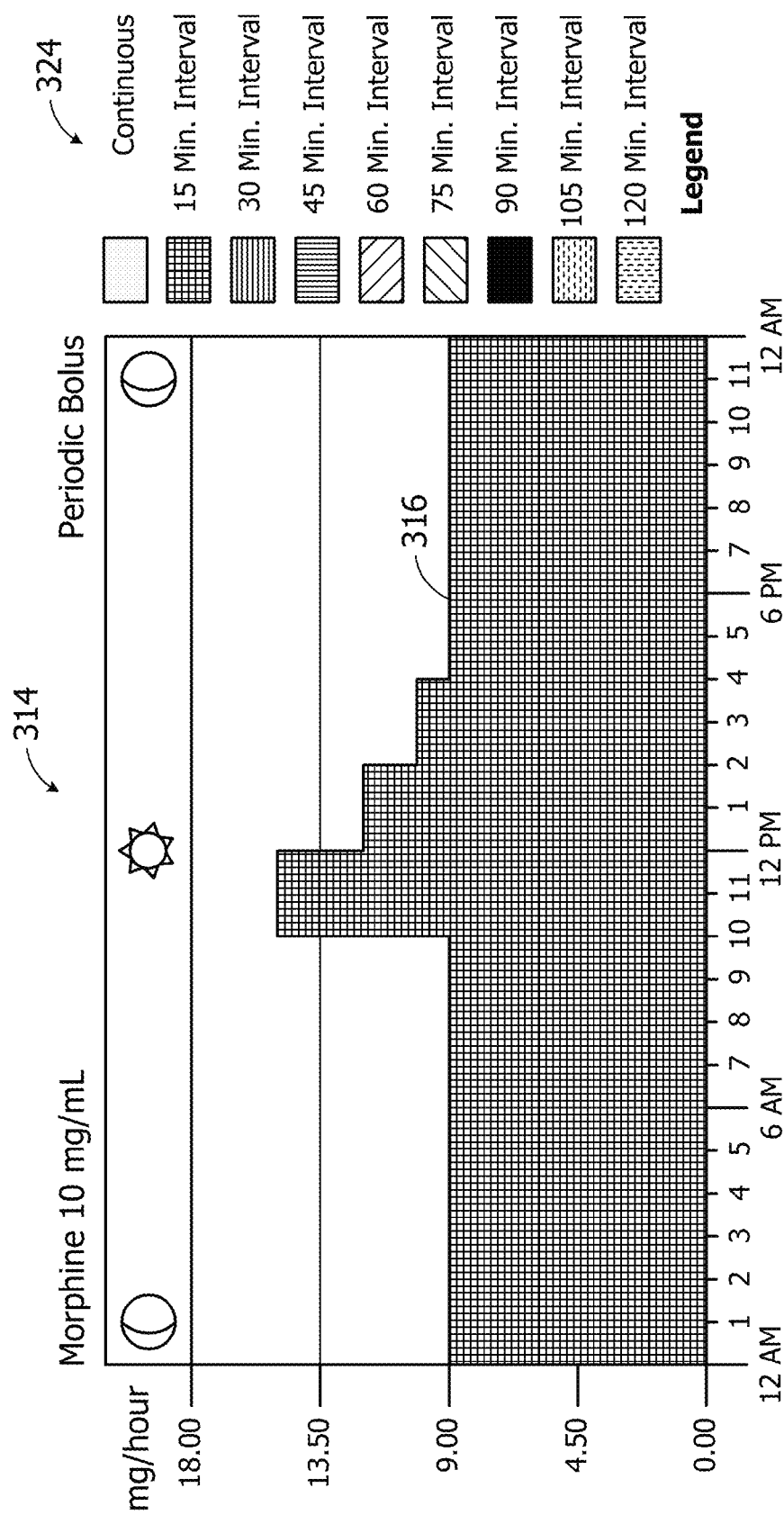
FIG. 20 is a graphical representation of a continuous-delivery delivery profile and a plurality of periodic bolus deliveries that may be displayed in accordance with one embodiment of a present invention.

Color may also be employed by the clinician's programming unit 200 to provide information to the clinician. As illustrated for example in FIG. 20, the color of the profile representation 316 may be changed from a color that represents continuous delivery (e.g. gray) to a color that represents the translation to a periodic bolus delivery as well as the bolus interval. In the exemplary implementation, a legend 324 is presented adjacent to the graph 314 on the display 204b in order to show the color/interval correspondence. Additionally, in some implementations, the clinician may be able to translate a continuous delivery profile into periodic boluses, switch from one bolus interval to another, and/or return to the continuous delivery profile, by simply clicking on the appropriate color in the legend.

Figure 21A:
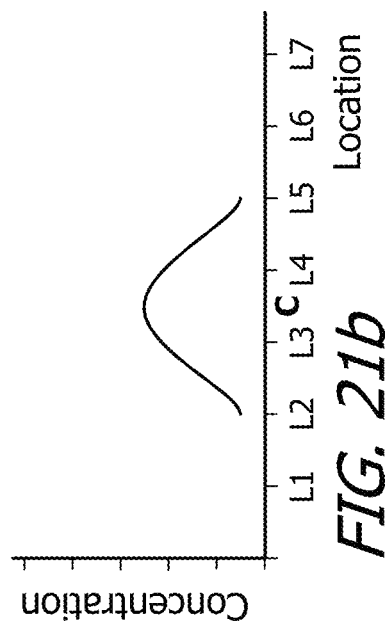
FIGS. 21a-21d are concentration versus location graphical representations of a bolus delivery that that may be displayed in accordance with one embodiment of a present invention.
Figure 21C:
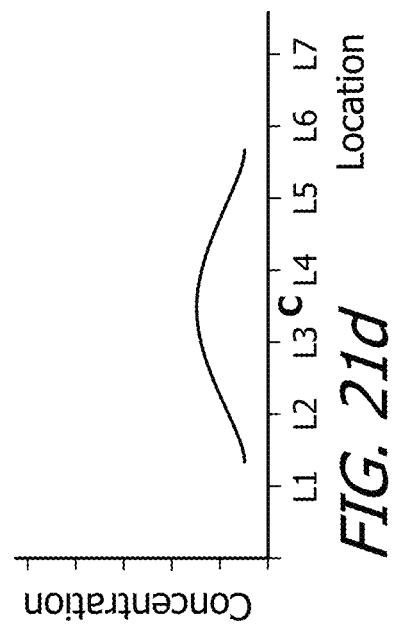
Figure 21B:
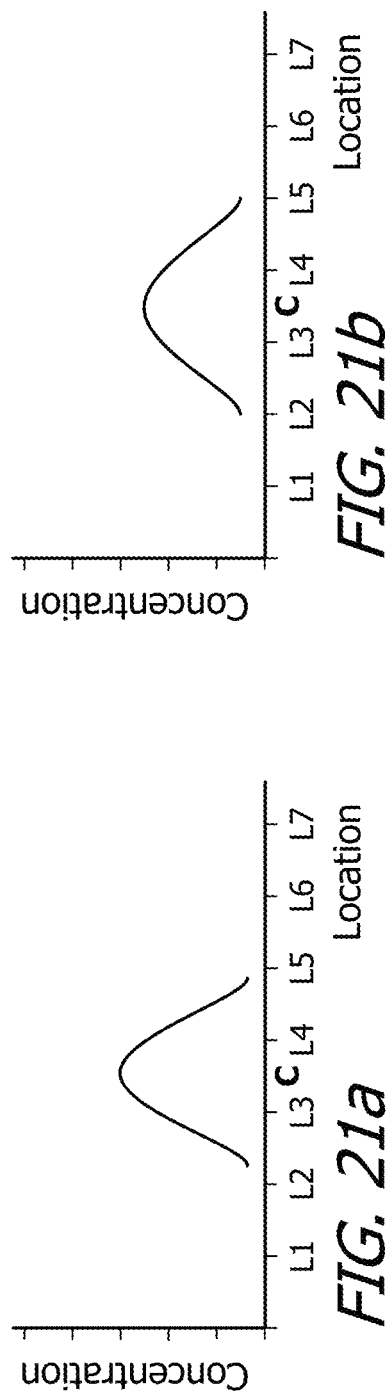
Figure 21D:
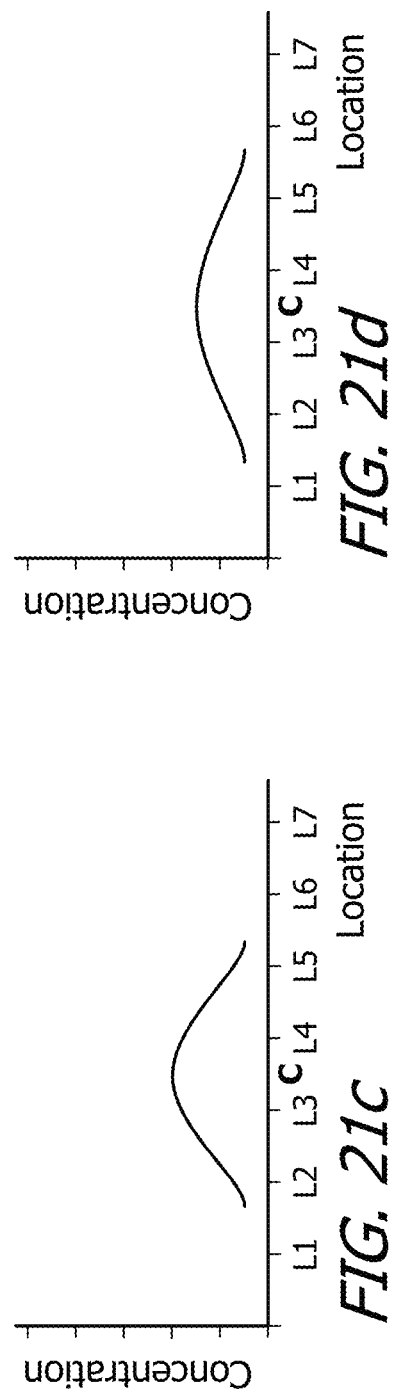
Figure 22:
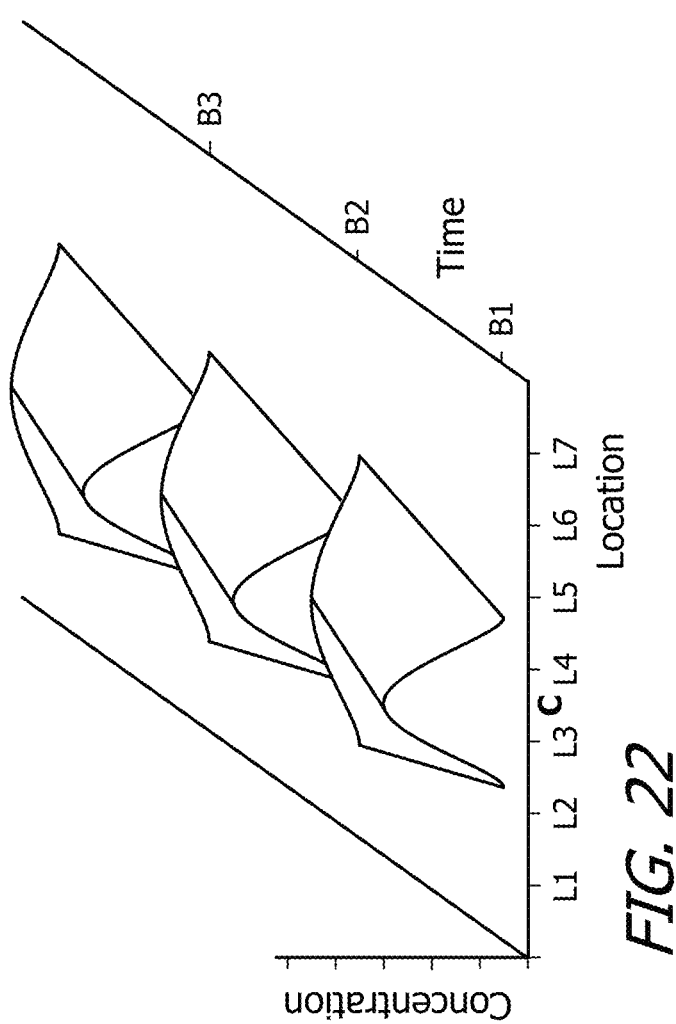
FIG. 22 is a concentration versus location versus time graphical representations of a plurality of bolus deliveries that that may be displayed in accordance with one embodiment of a present invention.

The clinician's programming unit 200 may also be used to display a graphical representation of the manner in which the infusible substance will disperse, based on the currently selected delivery method in order to assist the clinician's decision making process. The dispersal information may be experimentally derived for different combinations of location within the body (e.g. location within the CSF) and particular infusible substances. As illustrated for example in FIG. 21a, a concentration versus location graph 326 may employ a disbursement line 328 to illustrate how a particular bolus of an infusible substance will disburse when delivered to a particular location. In the exemplary implementation, seven locations L1-L7 are shown and the catheter outlet is represented by the "C." The disbursement line 328, which represents the concentration of the infusible substance, allows the clinician to see how the concentration of the infusible varies with location and to determine whether a particular bolus will have the intended effect on the intended tissue. Turning to FIGS. 21b-21d, the clinician may also be presented with a series of graphical representations, in a manner similar to time lapse photography, which shows how the disbursement of the infusible substance will change during the bolus interval. After reviewing the disbursement line 328 at the times, and in the states, represented in FIGS. 21a-21d, the clinician will know whether or not the selected bolus will disburse sufficiently to have the desired effect on all of the target tissue. Alternatively, as illustrated for example in FIG. 22, a three-dimensional concentration versus location versus time graph 330 may employ a disbursement topography 332 to illustrate how particular periodic boluses B1, B2, B3, etc. of an infusible substance will disburse when delivered to a particular location. Here too, upon review of the graph, the clinician will know whether or not the selected periodic bolus will disburse sufficiently to have the desired effect on all of the target tissue.

Although the inventions disclosed herein have been described in terms of the preferred embodiments above, numerous modifications and/or additions to the above-described preferred embodiments would be readily apparent to one skilled in the art. By way of example, but not limitation, the present inventions have application in infusion devices that include multiple reservoirs and/or outlets. It is intended that the scope of the present inventions extend to all such modifications and/or additions and that the scope of the present inventions is limited solely by the claims set forth below.

We claim:

1. A method of operating a clinician's programming unit, comprising the step of:
    displaying a graphical representation of a continuous-delivery delivery profile and a graphical representation of a plurality of periodic bolus deliveries with periods of non-delivery between successive bolus deliveries, which together are a translation of the continuous-delivery delivery profile, with the clinician's programming unit.

2. A method as claimed in claim 1, wherein the graphical representation of the periodic bolus deliveries comprises a plurality of spaced bolus markers superimposed over the graphical representation of the continuous-delivery delivery profile.

3. A method as claimed in claim 2, wherein spacing between the bolus markers is indicative of a bolus interval.

4. A method as claimed in claim 1, wherein the color of the graphical representation of a continuous-delivery delivery profile comprises the graphical representation of a plurality of periodic bolus deliveries with periods of non-delivery between successive bolus deliveries.

5. A method as claimed in claim 4, wherein the color of the graphical representation of a continuous-delivery delivery profile is indicative of a bolus interval.

6. A method as claimed in claim 1, further comprising the steps of:
    storing the continuous-delivery delivery profile;
    receiving a bolus interval; and
    translating the stored continuous-delivery delivery profile into a graphical representation of a plurality of periodic bolus deliveries with periods of non-delivery between successive bolus deliveries as a function of the received bolus interval with the clinician's programming unit.

7. A method as claimed in claim 6, further comprising the step of:
displaying an interval menu;
wherein the step of receiving a bolus interval comprises receiving a bolus interval by way of the displayed interval menu.

8. A method of operating a clinician's programming unit with a display, the method comprising the steps of:
receiving a bolus interval with the clinician's programming unit; and
displaying a graphical representation of a plurality of periodic bolus deliveries and periods of non-delivery between successive bolus deliveries that together are a translation of a stored continuous-delivery delivery profile, as a function of the received bolus interval, with the clinician's programming unit display.

9. A method as claimed in claim 8, further comprising the step of:
in response to an adjustment to the displayed graphical representation of a plurality of periodic bolus deliveries and periods of non-delivery between successive bolus deliveries, displaying a revised graphical representation of a plurality of periodic bolus deliveries and periods of non-delivery between successive bolus deliveries.

10. A method as claimed in claim 8, wherein the graphical representation includes a bolus interval representation, the method further comprising the step of:
in response to an adjustment of the displayed bolus interval representation to a revised displayed bolus interval representation, displaying a revised graphical representation of a plurality of periodic bolus deliveries and periods of non-delivery between successive bolus deliveries that are a translation of a stored continuous-delivery delivery profile, based on the revised bolus interval, with the clinician's programming unit display.

11. A method as claimed in claim 8, wherein the continuous-delivery delivery profile is stored by the clinicians programming unit.

12. A method as claimed in claim 8, wherein the continuous-delivery delivery profile is stored by an ambulatory infusion device.

13. A method as claimed in claim 8, wherein the graphical representation of the periodic bolus deliveries comprises a plurality of spaced bolus markers superimposed over the graphical representation of the continuous-delivery delivery profile.

14. A method as claimed in claim 13, wherein spacing between the bolus markers is indicative of a bolus interval.

15. A method as claimed in claim 8, further comprising the step of:
translating the stored continuous-delivery delivery profile into a graphical representation of a plurality of periodic bolus deliveries and periods of non-delivery between successive bolus deliveries, as a function of the received bolus interval, with the clinician's programming unit.

16. A method as claimed in claim 8, further comprising the step of:
displaying an interval menu;
wherein the step of receiving a bolus interval comprises receiving a bolus interval by way of the displayed interval menu.

17. A method as claimed in claim 8, further comprising the step of:
displaying a graphical representation of the continuous-delivery delivery profile with the clinician's programming unit display in conjunction with the graphical representation of a plurality of periodic bolus deliveries and periods of non-delivery between successive bolus deliveries.

\* \* \* \* \*